United States Patent [19]

Miners

[11] Patent Number: 4,505,146

[45] Date of Patent: Mar. 19, 1985

[54] PORTABLE SF₆ DECOMPOSITION SENSOR

[75] Inventor: Kamal E. B. Miners, Niagara Falls, Canada

[73] Assignee: Allied Corporation, Morris Township, Morris County, N.J.

[21] Appl. No.: 505,017

[22] Filed: Jun. 16, 1983

[51] Int. Cl.³ .............................................. G01N 27/12
[52] U.S. Cl. .............................................. 73/19; 73/23
[58] Field of Search ................ 73/19, 23; 422/98; 436/7, 119, 120

[56] References Cited

U.S. PATENT DOCUMENTS

| | | | |
|---|---|---|---|
| 3,512,939 | 5/1970 | Hugi | 422/86 |
| 3,680,359 | 8/1972 | Lynch | 73/23 |
| 4,112,737 | 9/1978 | Morgan | 73/19 |
| 4,394,635 | 7/1983 | Foss | 73/19 |
| 4,436,699 | 3/1984 | Narato et al. | 422/98 |

FOREIGN PATENT DOCUMENTS 2854628 6/1980 Fed. Rep. of Germany .
47-11478 4/1972 Japan .

Primary Examiner—Stephen A. Kreitman
Attorney, Agent, or Firm—Arthur J. Plantamura; Jay P. Friedenson

[57] ABSTRACT

A portable gas analyzer is provided for detecting SF₆ decomposition products in electrical equipment to signal a warning before decomposition reaches the stage that the presence of the decomposition products causes degradation of the solid insulating materials used in the construction of the SF₆ equipment. The forewarning of the decomposition products anticipates costly breakdowns. The portable gas analyzer is based on the principle of non-destructive testing wherein the surface sensitivity of selected insulating materials which decrease rapidly when exposed to increasing concentrations of SF₆ decomposition products is measured.

4 Claims, 2 Drawing Figures

PORTABLE SF$_6$ DECOMPOSITION SENSOR

DESCRIPTION

The invention relates to a portable testing device for use with electrical apparatus that contains a gaseous filling medium consisting at least partly of sulfur hexafluoride (SF$_6$) to detect SF$_6$ decomposition products. Corona or other abnormal conditions in such equipment during use generate SF$_6$ decomposition products which, over an extended period of time if not corrected, will accelerate the degradation of the solid insulating materials used in the construction of the electrical equipment and result in consequential damage and often prolonged costly downtime to the equipment.

BACKGROUND OF THE INVENTION

It is known that gaseous contaminants usually by deterioration can occur in the SF$_6$ gas composition used as insulation in such appliances. In addition to humidity which finds its way into the insulating gas and is a pronounced problem contributing to the decomposition products of the sulfur hexafluoride (SF$_6$), secondary reaction products of these decomposition products are formed with the substances present in the electrical appliance. These decomposition consequences are caused by electrical discharges, which in some cases occur in normal operation, as in switches, and in some cases only when a defect develops, as in transformers. The gaseous contaminants which occur as a result of decomposition of the SF$_6$, i.e., the decomposition products themselves and their secondary reaction products, are undesirable since they attack the materials used in the appliance, and thus also impair the insulation, consequently endangering the reliability of the appliance. While analysis of SF$_6$ gas samples taken from electrical equipment to determine the presence therein of SF$_6$ decomposition products and their concentrations have been conducted in the past, the more reliable techniques have been limited to laboratory application. In such situations, the time which elapses between the time of collection of an SF$_6$ sample from the field and the time when practical analysis in the laboratory can be effected has been shown to be important especially when dealing with very low concentrations of SF$_6$ by-products.

Also while devices for monitoring decomposition products are known such as that of U.S. Pat. No. 3,512,939 and Japanese Patent Application Publication No. 47-11478, both of which rely on a color change in the instrument to signal the presence of SF$_6$ decomposition products, no device is known which provides a simple and easy to use portable tool for use on the site that provides a reliable readout of the degree of SF$_6$ decomposition products which are present in low levels in the SF$_6$ insulating gas. For example, the device of the Japanese application can only detect SF$_6$ decomposition products that result in forming fluorine or hydrogen fluoride reaction products. Also the sensitivity of that device is low due to the dependence on the presence of fluorine and hydrogen fluoride in the SF$_6$ gas to provide a measurement.

It is, therefore, apparent that a need exists for a portable analyzer which detects, in situ, the level of SF$_6$ gas decomposition products in operating electrical apparatus that use SF$_6$ gas as an insulating medium to provide timely and reliable warning based on early detection of SF$_6$ decomposition that the equipment should be serviced before costly breakdown occurs.

SUMMARY OF THIS INVENTION

The invention relates to a portable hand-held device that senses the level of SF$_6$ gas decomposition products that are present in electrical apparatus based on surface sensitivity that is present in a sample drawn from the electrical equipment.

Corona or other abnormal conditions may generate small quantities of SF$_6$ decomposition products, which, while having an insignificant immediate impact on the electrical integrity of the system, in the long run cause degradation of solid insulating materials which in turn lead to electrical failure and expensive, unscheduled shutdown if not remedied in time.

The portable SF$_6$ decomposition detecting device provided by the invention is based on the principle of non-destructive testing wherein surface sensitivity of selected insulating materials that decreases rapidly when exposed to increased concentrations of SF$_6$ decomposition products is measured. The device comprises:

A sampling means such as a value that can be adapted to the electrical gas insulated equipment in the field to secure a sample.

A vacuum pump that is preferably part of the portable device, although it may be a separate accessory, and which is capable of efficiently evacuating the testing device to a level of the order of 100 microns or less.

A test chamber which may be easily assembled in the field to insert a test cartridge comprised of a material, e.g. a resin, that is sensitive to surface degradation from SF$_6$ by-products.

A pressure gauge to detect the pressure reading as the sample is taken from the apparatus to be tested.

A variable current limiting resistance element to permit calibration of the device.

A variable high voltage DC power supply to activate the unit and provide a reading of the electrical sensitivity effects of the SF$_6$ by-products on the cartridge, i.e., detect the relative change in the SF$_6$ resulting from deterioration of SF$_6$, and a nano-ammeter (or other recording device) to visually or graphically record the resultant electrical sensitivity and provide an indication of the level of SF$_6$ by-products present in the SF$_6$ insulation gas.

DESCRIPTION OF THE PREFERRED EMBODIMENTS

The portable gas analyzer of the invention, in sensing the degree of decomposition of the insulating SF$_6$ containing gas composition being tested, measures the surface resistivity of selected insulating materials, the resistivity of which decreases rapidly when exposed to increasing concentrations of SF$_6$ decomposition products.

SF$_6$ is a known insulator for high voltage electrical apparatus. When subjected in the electrical equipment to various conditions of high electrical fields, such as heat, corona effects, electric arc and the like, the SF$_6$ gas tends to decompose. Under such conditions, significant amounts of the SF$_6$ are converted to a variety of by-products such as SF$_4$, SF$_2$, S$_2$F$_2$, SO$_2$F$_2$, SOF$_2$, S$_2$F$_{10}$, and the like. A number of such by-products have a substantial corrosive effect which not only harms the equipment, and may result in electrical power interruption due to failure, but also has the disadvantage in that such by-products are often a hazard in the workplace.

The portable device of the invention is devised to be readily transported to the site of the electrical equipment, to be connected to the electrical system containing the gas to be examined, and to measure the properties of the SF$_6$ gas promptly and conveniently. The results derived from the test readings of the apparatus serve as an important aid in preventive maintenance of the equipment.

Figure 1:
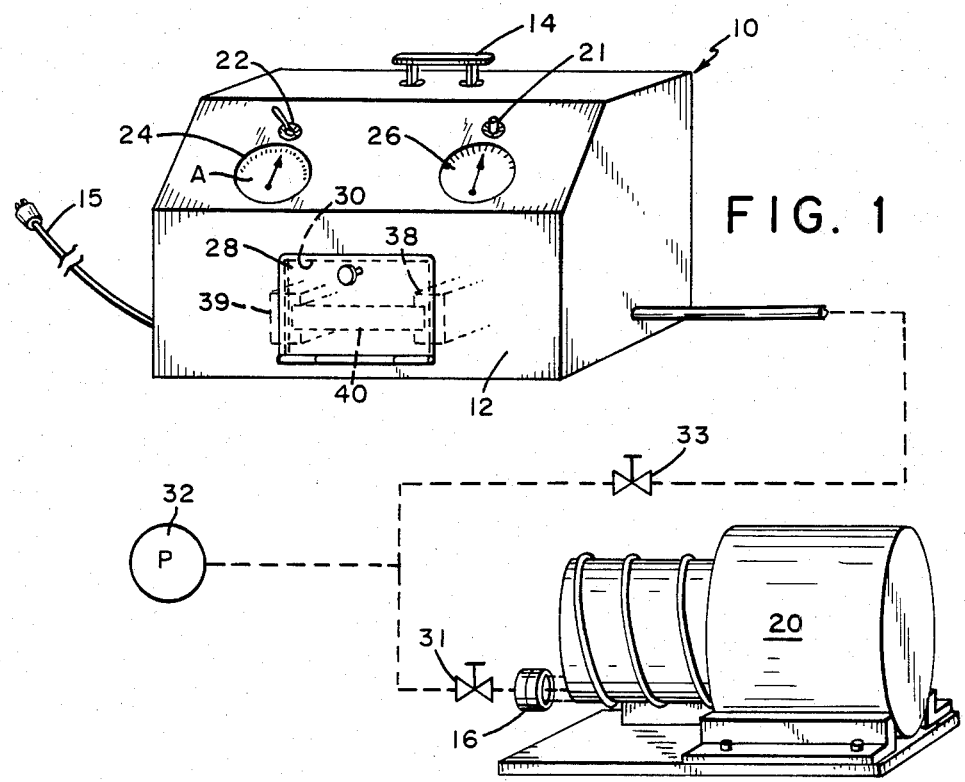
FIG. 1 is a perspective illustration of the portable gas analyzer device according to the invention showing a means to connect the device to receive a sample of the gas from the electrical equipment, calibrating means and means to obtain a readout of the resistivity of the sample SF$_6$ gas.

Referring to FIG. 1 of the drawing the portable device 10 of the invention comprises a suitable cabinet 12 to house the several parts, to be detailed hereinafter. As shown in FIG. 1, the housing 12 is provided with a carrying handle 14 and a quick disconnect coupling 16 to connect the portable device to a mating coupling on a SF$_6$ gas access port (not shown) of the electrical apparatus (shown generally as 20) whose SF$_6$ gas property is to be analyzed.

The housing 12 of the tester 10 is provided with a suitable power supply which may be self-contained or supplied via a transformer from the line 15. A switch 22 is provided to allow the unit to be calibrated to a uniform setting before each test. Also shown on the housing 12 is a nano-ammeter 24 which provides a reading in nanoamperes of the leakage current and a compound pressure gauge 26 to show the gas pressure of the system and thereby to again allow the system to be adjusted to a given pressure or to be extrapolated so as to provide zero setting readings. A suitable access to the test compartment is shown at 30 into which a disposable single use cartridge is inserted and removed for each test. The compartment 30 is suitably formed for easily inserting a test cartridge 40 and may have any suitable construction. The compartment is preferably closed off such as by access doors 28 and 29 which may be spring loaded (not shown) so as to be normally in a closed position and opened only when inserting and removing a cartridge.

Figure 2:
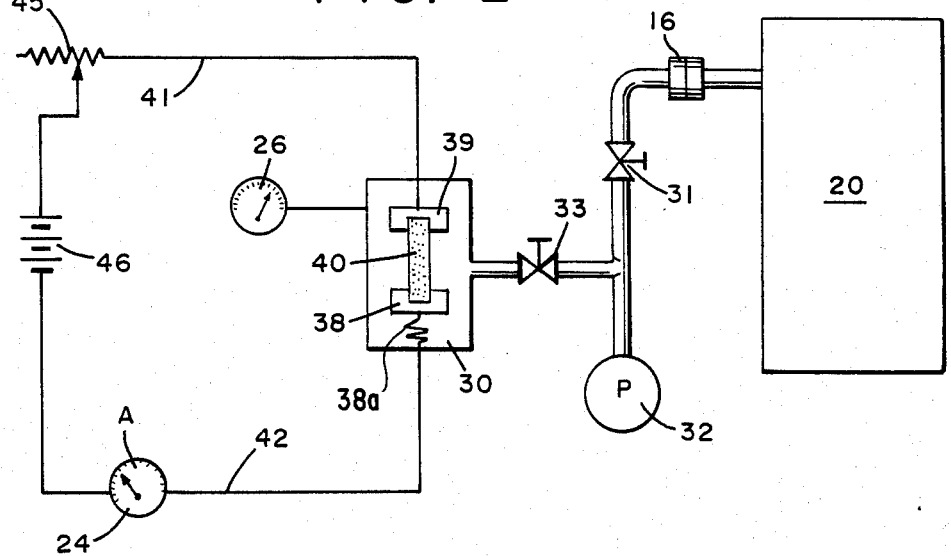
FIG. 2 is a schematic of the portable device illustrating diagrammatically the several components of the portable gas analyzer.

As shown in greater detail in FIG. 2, the portable tester of the invention comprises the connector 16 referred to in FIG. 1 connected to the tester 10 by means of a sampling valve 31. The tester includes a vacuum pump 32 and a test chamber isolating valve 33. The test chamber 30 is suitably formed so as to allow easy access for insertion and removal of test cartridges in the field and is formed of a material such as stainless steel, which has a high resistance to SF$_6$ by-products. Housed in the chamber 30 are means to hold a test cartridge 40 between a low voltage contact holder 38 and a high voltage contact holder 39. Electric conductors 41 and 42 are suitably insulated at entry points to the chamber 30. As shown, the contact holder 38 may be mounted on a compression spring 38$a$ to enhance contact of the test cartridge in said contacts. A variable current limiting resistance element shown at 45 is employed to provide a zero setting for the test. A DC power supply is shown as 46.

The test cartridge 40 is formed of a selected insulating material. For this purpose any of various materials such as pyrex glass or glazed or unglazed electrical porcelain as well as plastic materials such as an epoxy or other resin whose resistivity is sensitive to SF$_6$ by-products may be used. Such materials when subjected in the test chamber to various levels of SF$_6$ by-products, will provide correspondingly varying resistivities. The resistivity of the selected cartridge material is previously calibrated for different concentrations of SF$_6$ by-products. For this purpose for example, a pyrex disc formed from pyrex of the kind used by the Brown-Bovari Company as insulating support in electrical apparatus was employed between the contact holders 38 and 39 as the test cartridge 40. Also employed as the test material for the cartridge was glazed and unglazed electrical porcelain of the kind used in 345 kV Westinghouse or Brown-Bovari gas circuit breakers. In each case the exposure to SF$_6$ decomposition products resulted in a noticeable change in electrical resistivity as well as produced a surface erosion of the test element in the cartridge.

In operation the tester of the invention is connected to the electrical apparatus 20 whose SF$_6$ insulating gas is to be tested. A cartridge 40 is inserted in the chamber 30, valve 31 is closed, valve 33 opened and the chamber evacuated by pump 32. Power switch 21 is actuated and by means of switch 22, the unit is calibrated to a predetermined zero setting to accommodate for variations in the cartridge compaction resistivity. The valve 31 is then opened and, with power switch 21 closed, SF$_6$ gas from the system 20 is allowed to enter the chamber 30. Switch 21 is spring actuated as a safety measure to allow power to the system only when the switch 21 is depressed. The pressure at 26 is either controlled to a specified reading or the pressure is noted and extrapolated to a zero setting by reference to a table. When the power switch 21 is depressed allowing power to surge through the high voltage contact 39 to the cartridge 40, a reading of the change in resistivity is obtained at 24. A deviation of the order of about 100 or more nanoamperes would reflect the decrease in value of the resistivity and is a direct indication of the contamination.

Details hereinabove recited are provided to enable a fuller understanding of the invention. It will be understood, however, that such details except as required by the expressions in the claims should not be construed as a limitation of the invention.

What is claimed is:

1. A portable apparatus for detecting the degree of SF$_6$ gas decontamination present in electrical equipment comprising means to connect and obtain a sample of SF$_6$ gas from said equipment; a test chamber into which said sample in a measure quantity is introduced; a test cartridge of a composition sensitive to, and whose electrical resistivity is altered by exposure to, SF$_6$ gas by-products mounted in said chamber between a low voltage contact and a high voltage contact; a direct current power source connected to said high voltage contact; and a nano-ammeter connected to said low voltage contact to detect the change in resistivity through said cartridge when a power supply is introduced through said high voltage contact.

2. The apparatus of claim 1 which is further provided with a variable current limiting resistance element to calibrate the electrical power introduced to the high voltage contact.

3. The apparatus of claim 1 which includes in combination a vacuum pump and shutoff valves connected thereto whereby said valves allow the test chamber to be evacuated while connection to the electrical equipment is closed and thereafter said valves permit filling of the evacuated test chamber.

4. The apparatus of claim 1 wherein one of said cartridge holders is mounted on a compression spring to enhance contact of the test cartridge in said high voltage and low voltage contacts.

* * * * *